United States Patent [19]

Johnson et al.

[11] Patent Number: 4,558,165

[45] Date of Patent: Dec. 10, 1985

[54] CHROMIUM PHOSPHATE CATALYST

[75] Inventors: Marvin M. Johnson; Gerhard P. Nowack, both of Bartlesville, Okla.

[73] Assignee: Phillips Petroleum Company, Bartlesville, Okla.

[21] Appl. No.: 725,052

[22] Filed: Apr. 19, 1985

Related U.S. Application Data

[62] Division of Ser. No. 578,394, Feb. 9, 1984.

[51] Int. Cl.$^4$ .............................................. C07C 41/09
[52] U.S. Cl. ..................................... 568/698; 502/210
[58] Field of Search ........................................ 568/698

[56] References Cited

U.S. PATENT DOCUMENTS

| | | | |
|---|---|---|---|
| 3,965,208 | 6/1976 | Butter et al. | 260/671 M |
| 4,250,345 | 2/1981 | Chu | 585/467 |
| 4,259,537 | 3/1981 | Chu | 585/467 |
| 4,290,914 | 9/1981 | Katzen et al. | 502/162 |

FOREIGN PATENT DOCUMENTS 327382  3/1930  United Kingdom ................ 585/466

*Primary Examiner*—Howard T. Mars
*Attorney, Agent, or Firm*—L. M. Lavin

[57] ABSTRACT

An amorphous chromium (III) phosphate catalyst is used in alkylating aromatics and in the dehydration of alcohols to ethers.

7 Claims, No Drawings

CHROMIUM PHOSPHATE CATALYST

This application is a divisional application of my co-pending application Ser. No. 578,394, filed Feb. 9, 1984.

This invention relates to metal phosphates. In particular it relates to the use of chromium (III) phosphates as catalysts in the alkylation of aromatic hydrocarbons. It also relates to the use of chromium (III) phosphates as catalysts in the dehydration of alcohols to ethers. In particular, it relates to the use of chromium (III) phosphate as a catalyst used in the methylation of toluene and in the dehydration of methanol to dimethyl ether.

BACKGROUND OF THE INVENTION

In order to alkylate aromatic hydrocarbons, it is necessary that an alkylating agent be present. Alcohols can serve as alkylating agents.

Therefore, in a feed stream of alcohols and aromatic hydrocarbons, the dehydration reaction of the alcohol occurs at the same time the alkylation reaction occurs. Since xylene, an alkylated aromatic, is a preferred product, the alkylation reaction is the preferred reaction and catalysts are chosen because of their ability to hinder the dehydration reaction and advance the alkylation reaction. The dehydration reaction will occur, however, using the same catalyst.

The alkylation of aromatic hydrocarbons utilizing crystalline catalysts is well known in the art. The alkylation process is used to produce xylenes. Xylenes come in three isomeric forms: ortho-, meta- and para-xylene, the latter of which is of particular value in the manufacture of terephthalic acid which is an intermediate in the manufacture of synthetic fibers such as poly(ethylene terephthalate).

Prior art has shown the use of crystalline aluminosilicate catalysts in the production of xylenes through aromatic alkylation. One problem with some of these catalysts is that they tend to lose their activity quickly. These catalysts must also be selective. The reaction must favor particularly desired compounds, for instance para-xylenes over ortho-or meta-xylenes. It must also give reasonably high conversion rates.

Therefore, an object of this invention is to provide a catalyst that would not lose activity quickly.

Another object of this invention is to provide a selective catalyst. A preferred object of this invention is to provide a catalyst selective to para-xylene.

Another object of this invention is to provide a catalyst that provides high conversion rates.

Another object of this invention is to provide a catalyst that increases the production of alkyl-substituted aromatic hydrocarbons.

A specific object is to provide a catalyst for the production of xylene.

Another object of this invention is to provide a catalyst for the dehydration reaction of alcohols.

Other objects will become apparent from the following descriptions.

SUMMARY OF THE INVENTION

In accordance with the present invention, metal phosphates have been discovered to be active catalysts for a variety of alkylation and dehydration processes. In particular, chromium (III) phosphates and combined chromium (III) aluminum phosphates are active for the alkylation of aromatic hydrocarbons and the dehydration of alcohols to ethers. In a specific embodiment, it has been discovered that chromium (III) and combined chromium (III) aluminum phosphates are active for the methylation of toluene with methanol and for the dehydration of methanol to dimethyl ether.

DETAILED DESCRIPTION OF THE INVENTION

Chromium (III) phosphates are prepared using conventional methods. One method for producing the chromium (III) phosphates of this invention includes precipitating from solutions of dissolved chromium (III) salts and phosphates or hydrogen phosphates, the solutions preferably being neutral or slightly basic.

The metal phosphate catalyst can possess any ratio of chromium to phosphate. The atomic ratio of chromium to phosphorus will preferably be greater than unity. More preferably, the atomic ratio of chromium to phosphorus will be about 1.2:1 to about 1.7:1.

The metal phosphate catalyst can be present with chromium (III) phosphate alone or in any combination of chromium (III) phosphate and aluminum phosphate. These metal phosphates can be present in any relative amounts, from entirely chromium phosphate to almost entirely aluminum phosphate.

The preferred combined chromium (III) aluminum phosphate can be prepared in any conventional manner. Preferably, the combined phosphate is prepared by coprecipitation of $Cr^{+3}$ ions and $Al^{+3}$ ions with $PO_4^{-3}$ or $HPO_4^{-2}$ ions in aqueous solutions.

The metal phosphate catalyst can also be attached to a hydroxide group. The following formula represents metal phosphate catalyst of this group:

$$Cr(PO_4)_n \cdot (OH)_m$$

wherein n can range from about 0.5 to abot 0.9 and m can range from about 1.5 to about 0.3.

The alkylation of aromatic hydrocarbons such as benzene or toluene to m-, o-, p-xylene can be carried out with linear or branched alcohols having 1 to 10 and preferably 1 to 4 carbon atoms per molecule. The presently preferred aromatic hydrocarbon is toluene and the presently preferred alcohol is methanol.

The alkylation of an aromatic hydrocarbon, in the presence of the metal phosphate catalyst, is effected by contact of the aromatic hydrocarbon with an alcohol, at a temperature between about 150° C. and 550° C. and preferably between about 350° C. and 500° C. The reaction generally takes place at a pressure from about 50 psig to about 800 psig, but preferably the pressure will be within the approximate range of 150 psig to about 600 psig.

The molar ratio of the alcohol to the aromatic hydrocarbon is generally between about 0.3:1 and about 3:1. When methanol is employed as an alkylating agent and toluene is used as the aromatic hydrocarbon, a suitable molar ratio of methanol to toluene has been found to be approximately 0.4:1 to 1.5:1 moles of methanol per mole of toluene.

The metal phosphate catalyst can be present in any suitable amount necessary for the alkylation of aromatic hydrocarbons and for the dehydration of alcohol. The reaction is suitably accomplished utilizing a liquid hourly space velocity (volume of feed/hour/volume of catalyst) of between about 1 and about 10 and preferably between about 2 and about 7.

The condensed product of the reaction of toluene and methanol comprising dimethyl ether, p-xylene, o-xylene, and m-xylene can be separated by any suitable means such as recrystallization at low temperature or selective adsorption (e.g., in a chromatographic column). Generally, more o-xylene is formed than either p-xylene or m-xylene.

The process of this invention may be carried out as a batch-type, semicontinuous, or continuous operation utilizing a fixed or moving bed catalyst system. The catalyst after use is conducted to a regeneration zone after which the regenerated catalyst is recycled to a conversion zone for further contacting with the toluene and methylating agent reactants. The metal phosphate catalyst can be partially regenerated by air oxidation of about 900° F. for about 16 hours.

The following examples will serve to illustrate the process of this invention without limiting the same.

EXAMPLE I

Catalyst Preparation

Control catalyst A, $Al(PO_4)$, was prepared by adding a solution of 115 g (1 mol) of $(NH_4)H_2PO_4$ in 1 L of water to 237 g (1 mol) of $NH_4Al(SO_4)_2$ in 1 L of water, giving a clear solution. Precipitation was attempted by urea hydrolysis. Thus, one mole of urea (60 g) was added and the solution warmed to 60° C. for 48 hours. Precipitation had still not occurred, so solid $(NH_4)_2CO_3$ was added over a 2 hour period to neutralize the solution. The resulting precipitate was collected by filtration, pulverized and washed with 1 L of dilute $NH_4HCO_3$ (10 g/L), then oven-dried and finally calcined at 315° C. (600° F.) for 5 hours. The resulting catalyst had a surface area of 72.3 $m^2/g$ and a pore volume of 2.16 ml/g. The catalyst was mostly amorphous, but X-ray diffraction analysis did indicate a small degree of crystallinity.

Invention catalyst B, 1 mole percent Cr on $Al(PO_4)$, was prepared by mixing 1230.5 g (3.3 mol) $Al(NO_3)_3.9H_2O$, 227.6 g (2.0 mol) $(NH_4)H_2PO_4$, and 15.6 g (0.04 mol) of $Cr(NO_3)_3.9H_2O$ with 75 mL of water, then heating the mixture until homogenous. An aliquot of 200 mL of the syrup thus obtained was blended with 90 mL of concentrated $NH_4OH$ and stirred vigorously. The resulting mixture was heated to about 80° C. and stirred while 27.6 g (0.46 mol) of urea were added. After about 45 minutes, gelation occurred. The resulting gel was allowed to age in a forced air oven at 80° C. until liquid phase was no longer observable. The residue was then washed 3 times with equal volumes of dilute ammoniacal $H_2O$, then once with water and finally 2 times with equal volumes of acetone. The washed material was dried overnight in the vacuum oven to give about 44 g of clear turquoise gelatinous beads. These were activated for 3 hours at 700° C. in an air atmosphere.

Invention catalyst C, $Cr(PO_4)_{0.7}(OH)_{0.9}$, was prepared by mixing a solution containing 123.5 g (0.5 mol) of $Cr(OAc)_3\cdot H_2O$ in about 1 L of water with a solution of 39.6 g (0.3 mol) of $(NH_4)_2HPO_4$ in about 300 mL of water in a 2 L round bottom flask equipped with a Dean-Stark trap. The solution was heated to boiling and about 650 mL of water collected, during which time a blue-green precipitate formed. The pot was cooled, about 450 mL of ethyl acetate was added, and the pot contents again heated to reflux. Azeotroped water was collected at the rate of about 30 mL per hour, over about 6 hours. The pot was again cooled, 300 mL of additional ethyl acetate were added, and the pot again warmed to reflux to remove remaining water. The majority of the added ethyl acetate was then distilled off, then vacuum was applied to aid removal of residual amounts of solvent. The residual blue-green solid was heated to about 480° C. in stages under an air flow and held at 480° C. for about 1.5 hours. Catalyst turned gray-black when the calcination temperature reached about 250° C. The resulting material was determined to have a surface area of 132 $m^2/g$ and a pore volume of 1.08 ml/g. Elemental analysis revealed a chromium content of 42.1 weight percent and phosphorus content of 17.6 weight percent. This corresponds to an atomic ratio of Cr:P of about 1.4:1.

Invention catalyst D, $Cr(PO_4)_{0.6}(OH)_{1.2}$, was prepared according to the procedure described above, except 46.2 g (0.35 mol) of $(NH_4)_2HPO_4$ was employed. The resulting catalyst is gray, has a surface area of 142 $m^2/g$, a pore volume of 1.15 ml/g and elemental analyses of 37.8 weight percent chromium and 13.8 weight percent phosphorus. This corresponds to an atomic ratio of Cr:P of about 1.6 to 1.

Invention Catalyst E, $Cr(PO_4)_{0.6}(OH)_{1.2}$, was prepared by blending a solution of 247 g (1 mol) of $Cr(OAc)_3\cdot H_2O$ in 300 mL water with a solution of 105.6 g (0.8 mol) of $(NH_4)_2HPO_4$ in 400 mL of water. The solution was boiled for about 30 minutes, when gelation occurred. The gel was placed in an evaporating dish and allowed to air dry in the hood over about 24 hours. The catalyst was further dried for about 8 hours in a forced draft oven at about 105° C. (220° F.). Finally, catalyst was calcined at about 480° C. for 2 hours. Catalyst was analyzed and found to have a surface area of 155 $m^2/g$, a pore volume of 0.25 ml/g. Elemental analysis revealed a chromium content of 39 weight percent and a phosphorus content of 13.9 weight percent. This corresponds to an atomic ratio of Cr:P of about 1.6:1.

EXAMPLE II

The various catalysts prepared as described above were tested for dehydration activity and activity for alkylation of toluene. In all cases, 20 mL of catalyst was loaded into the center of a ½" diameter metal tubular reactor with a pre-heat and post-reaction zone each packed with about 6" of glass beads. The reactor was brought up to reaction temperature under hydrogen pressure, then hydrogen feed discontinued and methanol or methanol/toluene feed started. Both liquid and gas samples were collected and analyzed by gas liquid chromatography. Reaction conditions and results are summarized in the Table.

TABLE

| Run # | Catalysts g | Feed mL/hr MeOH | Feed mL/hr Toluene | Reaction Conditions Temp, °C. | Reaction Conditions Press, psig | Conversion, % MeOH | Conversion, % Toluene | % Selectivity to $Me_2O$ | % Selectivity to Xylenes |
|---|---|---|---|---|---|---|---|---|---|
| 1 | A, 15.9 | 20 | 115 | 455 | 300 | >90 | <0.5 | >90 | ~85 |
| 2 | B, 10.2 | 20 | 115 | 455 | 300 | 100 | 16 | ~90 | 81[1] |
| 3 | C, 8.5 | 140 | — | 190 | 300 | 1.4 | — | ND | — |
| 4 |  | 120 | — | 370 | 300 | 40 | — | ~90 | — |

TABLE-continued

| Run # | Catalysts g | Feed mL/hr MeOH | Feed mL/hr Toluene | Reaction Conditions Temp, °C | Reaction Conditions Press, psig | Conversion, % MeOH | Conversion, % Toluene | % Selectivity to Me$_2$O | % Selectivity to Xylenes |
|---|---|---|---|---|---|---|---|---|---|
| 5 |  | 40 | — | 370 | 300 | 52 | — | >90 | — |
| 6 |  | 40 | — | 370 | 300 | 58 | — | >95 | — |
| 7 | E, 21 | 30 | 60 | 315 | 150 | low | low | ND | ND |
| 8 |  | 20 | 50 | 425 | 150 | >90 | 26 | >90 | 83 |
| 8A |  | 20 | 110 | 540 | 50 | ND | <0.5 | ND | ND |
| 9 | E, 22 | 20 | 90 | 425 | 300 | ND | 21 | ND | 78[2] |
| 10 |  | 30 | 95 | 425 | 600 | ND | 6.3 | ND | 87[2] |
| 11 |  | 30 | 100 | 410 | 300 | ND | 2.2 | ND | >90[2] |
| 12 |  | 30 | 100 | 410 | 300 | ND | 1.2 | ND | >90[2] |

[1]The composition of the xylenes was: about 29 weight-%-p-xylene, about 20 weight-% m-xylene and about 51 weight-% o-xylene.
[2]The composition of the xylenes was: about 33 weight-% p-xylenes, 22 weight-% m-xylenes and 44 weight-% o-xylenes.

The results of these experiments demonstrate that phosphate deficient chromium phosphate catalysts are active dehydration catalysts for alcohols and are active for the alkylation of aromatics such as toluene in the presence of alkylating agents such as methanol.

We claim:

1. A process for the dehydration of an alcohol to an ether comprising contacting said alcohol with a chromium (III) phosphate.

2. A process according to claim 1 where said chromium (III) phosphate is a combined chromium (III) aluminum phosphate.

3. A process according to claim 1 where said chromium (III) phosphate has a chromium to phosphorus ratio greater than unity.

4. A process according to claim 3 where said chromium to phosphorus ratio ranges from about 1.2:1 to about 1.7:1.

5. A process according to claim 1 where said chromium (III) phosphate is represented by the formula:

$$\mathrm{Cr\,(PO_4)_n\cdot(OH)_m}$$

where n ranges from about 0.5 to about 0.9 and m ranges from about 1.5 to about 0.3.

6. A process as in claim 1 where said alcohol is methanol.

7. A process according to claim 1 where said dehydration takes place with a liquid hourly space velocity of between about 1 and about 10.

* * * * *